US00PP14550P39

(12) United States Plant Patent
Moser

(10) Patent No.: US PP14,550 P3
(45) Date of Patent: Feb. 17, 2004

(54) CHRYSANTHEMUM PLANT NAMED 'MOZA LOT 01'

(50) Latin Name: *Chrysanthemum morifolium*
Varietal Denomination: Moza Lot 01

(75) Inventor: Frank Moser, Alva, FL (US)

(73) Assignee: Mozant, LLC, Oxnard, CA (US)

( * ) Notice: Subject to any disclaimer, the term of this patent is extended or adjusted under 35 U.S.C. 154(b) by 41 days.

(21) Appl. No.: 09/865,150

(22) Filed: May 24, 2001

(65) Prior Publication Data

US 2002/0178475 P1 Nov. 28, 2002

(51) Int. Cl.[7] ..... A01H 5/00
(52) U.S. Cl. ..... Plt./286
(58) Field of Search ..... Plt./291, 286, 297, Plt./293

(56) References Cited

PUBLICATIONS

"Chrysanthemum Leaf Classification", http://www.ee.surrey.ac.uk/Research/VSSP?demos/leaf/index.html., Jan. 2001.*

* cited by examiner

*Primary Examiner*—Anne Marie Grunberg
(74) *Attorney, Agent, or Firm*—Knobbe, Martens, Olson & Bear, LLP

(57) ABSTRACT

A new and distinct Chrysanthemum plant variety characterized by a daisy type inflorescence with pink/white color ray florets, consistent flowering response to short days, blooming consistently after 49 days of short day length, small foliage, short internode length, and consistent natural season flowering habit during late September.

2 Drawing Sheets

Latin name of the genus and species of the plant claimed: *Chrysanthemum morifolium.*
Variety denomination: 'Moza Lot 01.'

BACKGROUND OF THE INVENTION

The present invention relates to a new and distinct cultivar of Chrysanthemum plant, herein after referred to by the cultivar name 'Moza Lot 01.'

This new cultivar originated from hybridization of a female parent Chrysanthemum cultivar MZ 215-01 (unpatented, and undistributed commercially) and a male parent Chrysanthemum cultivar MZ 257-01 (unpatented in the United States, and undistributed commercially). The new cultivar was discovered by the inventor in November 1998.

Asexual reproduction of the new cultivar by apical tip cutting and meristem tissue culture was performed in Oxnard, Calif. and has shown that the unique features of this new cultivar are stable and reproduced true to type on successive generations.

SUMMARY OF THE INVENTION

The cultivar 'Moza Lot 01' has not been observed under all possible environmental conditions. The phenotype may vary somewhat with variations in environment such as temperature, daylength, and light intensity, without, however, any variance in genotype.

The following traits have been repeatedly observed and are determined to be the unique characteristics of 'Moza Lot 01.' These characteristics in combination distinguish 'Moza Lot 01' as a new and distinct Chrysanthemum:

1. Daisy type inflorescence with pink/white color ray florets;
2. Consistent flowering response to short days, blooming consistently after 49 days of short day length;

3. Small foliage;
4. Short internode length; and
5. Consistent natural season flowering habit during late September.

Plants of the new cultivar are similar to plants of the female parent cultivar in most horticultural characteristics, however plants of the new cultivar differed from plants of the female parent cultivar in the following characteristics:

1. The new cultivar has different color ray florets;
2. The new cultivar is taller; and
3. The new cultivar has a more flexible plant shape.

Plants of the new cultivar are similar to plants of the male parent cultivar in most horticultural characteristics, however plants of the new cultivar differed from plants of the male parent cultivar in the following characteristics:

1. The new cultivar has different color ray florets;
2. The new cultivar is taller; and
3. The new cultivar naturally blooms 2 weeks later.

BRIEF DESCRIPTION OF THE PHOTOGRAPHS

DETAILED BOTANICAL DESCRIPTION

Figure 1:
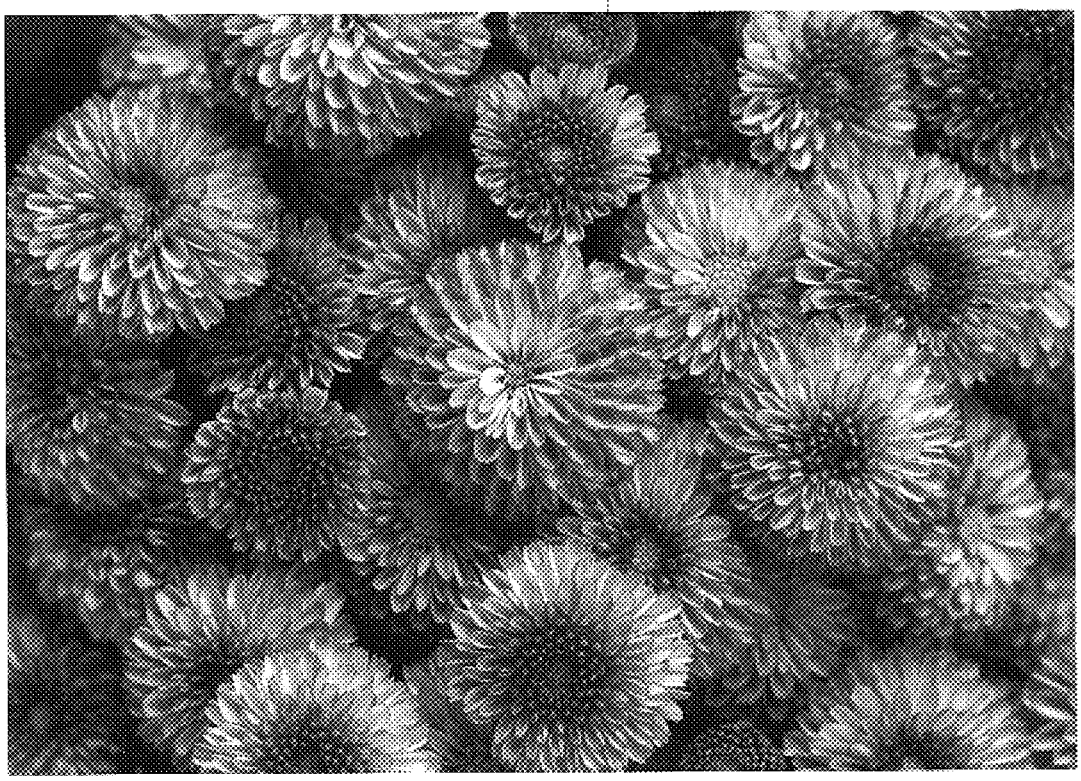
FIG. 1 shows a close up view of the flowers and buds of the new cultivar.
Figure 2:
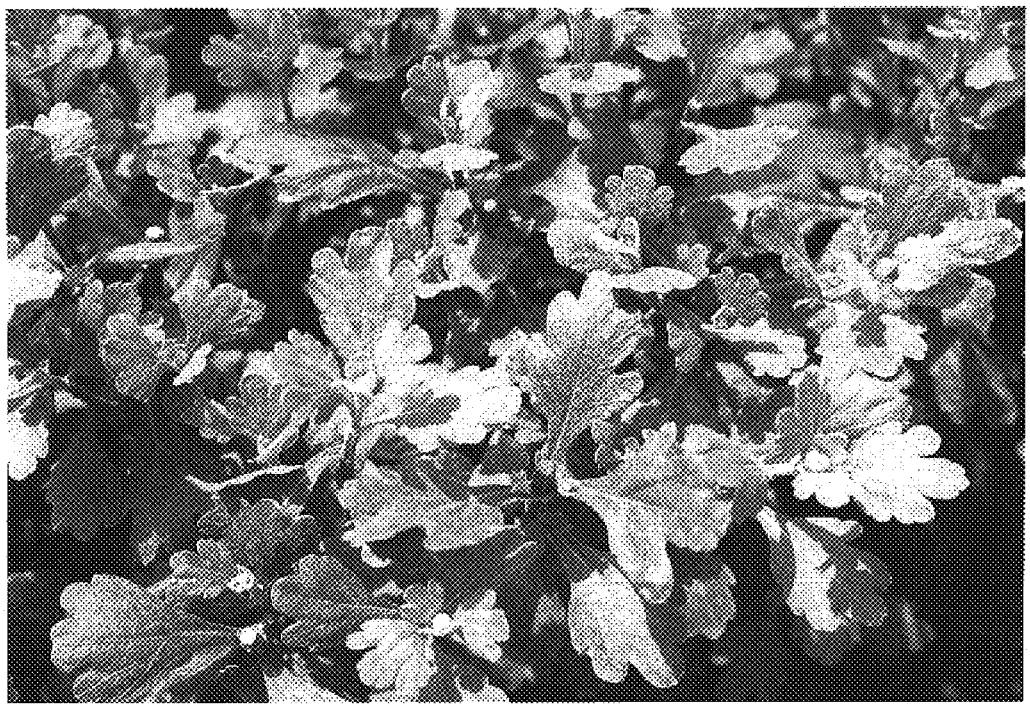
FIG. 2 shows the foliage of the new cultivar.

In the following description, color references are made to The Royal Horticultural Society Colour Chart except where general terms of ordinary dictionary significance are used. The following observations and measurements describe plants grown in a commercial filed on Oxnard, Calif. in the month of September 2000. The plant described is approximately 95 days old, and was grown from a rooted cutting given one pinch after 10 days from planting. There was no spray or disbud treatment given. The growing conditions range from 60° to 65° F. at night to 70° to 85° during the day. Measurements and numerical values represent averages of typical flowering types.

Botanical classification: *Chrysanthemum morifolium* cultivar 'Moza Lot 01'.

Commercial classification: Garden-type Chrysanthemum.

Parentage: Hybridization of female parent Chrysanthemum cultivar (unpatented in the United States) with a male parent Chrysanthemum cultivar (unpatented in the United States).

Commercial comparison: Comparison variety "Roadrunner" U.S. Plant Pat. No. 11,298, the most similar multi-color ray floret variety. The new variety differs from Roadrunner in having a later natural season bloom time, smaller diameter inflorescence, pink/white ray florets as opposed to red/yellow ray florets, more ray florets and more disc florets than Roadrunner.

PROPAGATION

*Time to rooting.*—7 to 14 days at approximately 21° C.
*Rooting habit.*—Fine, fibrous.

PLANT

*Growth habit.*—Mounding herbaceous perennial.
*Height.*—Approximately 22 cm.
*Branching characteristics.*—Moderate Branching.
*Internode length.*—Approximately 2.7 cm.
*Length of lateral branches.*—Approximately 16 cm.
*Number of leaves per lateral branch.*—Approximately 14 .
*Stem Color.*—Near 138A.

FOLIAGE

Leaf:
*Arrangement.*—Alternate single.
*Average length.*—Approximately 6.1 cm.
*Average width.*—Approximately 3.4 cm.
*Shape of blade.*—Ovate.
*Apex.*—Acuminate.
*Base.*—Attenuate.
*Attachment.*—Stalked.
*Margin.*—Serrate.
*Texture of top surface.*—Lightly pubescent.
*Texture of bottom surface.*—Lightly pubescent.
*Color.*—Young foliage upper side: Near 138A. Young foliage under side: Near 138B. Mature foliage upper side: Near 138A. Mature foliage under side: Near 138B. Venation upper side: Near 138C. Venation under side: Near 137C.

Petiole:
*Average length.*—Approximately 2.0 cm.
*Petiole color.*—Approximately 137C.

BLOOM

Inflorescence:
*Flowering habit.*—Induced by darkness period greater than 13.5 hours, blooming consistently after 49 days of appropriate day length required to induce and develop blooms.
*Inflorescence form.*—Daisy.
*Natural flowering season.*—Approximately the last two weeks in September.
*Number of inflorescences per stem.*—Approximately 17.
*Inflorescence diameter.*—Approximately 3.1 cm.
*Inflorescence depth.*—Approximately 2.2 cm.
*Inflorescence longevity on plant.*—Approximately 24–29 days.
*Persistence.*—Persistent.
*Fragrance.*—Not Present.

Ray florets:
*Appearance.*—Matte.
*Texture.*—Smooth.
*Average number per flower.*—Approximately 320.
*Shape.*—Oblanceolate.
*Margin.*—Entire.
*Apex.*—3 acute lobes.
*Length.*—Approximately 1.5 cm.
*Width.*—Approximately 0.5 cm.
*Color.*—Upper surface at first opening: Near 53D. Upper surface at maturity: Near 51D at the tip; Near 36D at the base. Upper surface at fading: Near 65B at the tip; Near 155D at the base. Under surface at first opening: Near 54A. Under surface at maturity: Near 54C at the tip; Near 155D at the base. Under surface at fading: Near 56A at the tip; Near 155D at the base.

Disc florets:
*Appearance.*—Shiny.
*Texture.*—Smooth.
*Average number per flower.*—Approximately 100.
*Shape.*—Cylindric.
*Apex.*—Obtuse.
*Average length.*—Approximately 0.7 cm.
*Average width.*—Approximately 0.1 cm.
*Color.*—At first opening: Near 13A. At maturity: Near 13B. At fading: Near 15C.

Peduncle:
*Length.*—At terminal end (shortest): Approximately 4 cm. At lateral end (longest): Approximately 7 cm.
*Strength.*—Moderate.
*Color.*—Near 138B.
*Habit.*—Erect.

Inflorescence bud:
*Length.*—Approximately 0.6 cm.
*Diameter.*—Approximately 0.6 cm.
*Form*—Globular.
*Color.*—Near 51B.

Sepals:
*Appearance.*—Matte.
*Texture.*—Lightly pubescent.
*Number.*—Approximately 20 to 30.
*Shape.*—Ovate.
*Margin.*—Entire.
*Apex.*—Acute.
*Color.*—Upper side: Near 138A. Under side: Near 138A.

REPRODUCTIVE ORGANS

Ray florets:
*Number of pistils per floret.*—1.
*Stigma shape.*—2 branched.
*Stigma color.*—Near 16D.
*Style color.*—Near 7A.
*Style length.*—Approximately 0.4 cm.
*Number of stamens per floret.*—Absent.

Disc florets:
*Number of pistils per floret.*—1.
*Stigma shape.*—Cylindric.
*Style length.*—Approximately 0.3 cm.
*Stigma color.*—Near 1A.

*Style color.*—Near 3D.
*Number of stamens per flower.*—Approximately 5.
*Anther shape.*—Tubular.
*Anther color.*—Near 12A.
*Pollen color.*—Near 13A.

OTHER CHARACTERISTICS

Seed production: Commercially, this plant is not used or observed in a stage wherein seeds would be produced. Therefore, seed production has not been observed.

Disease resistance: Neither resistance nor susceptibility to diseases and pests have been observed in this cultivar.

What is claimed is:

1. A new and distinct variety of Chrysanthemum plant named 'Moza Lot 01' as herein illustrated and described.

* * * * *